(12) United States Patent
Jonsson

(10) Patent No.: US 9,993,357 B2
(45) Date of Patent: Jun. 12, 2018

(54) PROSTHETIC SOCKET SYSTEM

(71) Applicant: OSSUR HF, Reykjavik (IS)

(72) Inventor: Grimur Jonsson, Vogar (IS)

(73) Assignee: OSSUR HF, Reykjavik (IS)

( * ) Notice: Subject to any disclaimer, the term of this patent is extended or adjusted under 35 U.S.C. 154(b) by 0 days. days.

(21) Appl. No.: 14/627,574

(22) Filed: Feb. 20, 2015

(65) Prior Publication Data
US 2015/0238330 A1 Aug. 27, 2015

Related U.S. Application Data

(60) Provisional application No. 61/942,939, filed on Feb. 21, 2014.

(51) Int. Cl.
*A61F 2/80* (2006.01)
*A61F 2/78* (2006.01)
(Continued)

(52) U.S. Cl.
CPC .................. *A61F 2/80* (2013.01); *A61F 2/78* (2013.01); *A61F 2/7812* (2013.01); *A61F 7/02* (2013.01);
(Continued)

(58) Field of Classification Search
CPC .. A61F 2/78; A61F 2/7843; A61F 2/80; A61F 2002/802; A61F 2002/805; A61F 2002/807; A61F 2007/0051; A61F 2007/0057; A61F 2007/0058; A61F 2007/0063; A61F 2007/0068; A61F 2007/0075; A61F 2007/0244;
(Continued)

(56) References Cited

U.S. PATENT DOCUMENTS

| 708,685 A | 9/1902 | White |
|---|---|---|
| 4,655,779 A | 4/1987 | Janowiak |

(Continued)

FOREIGN PATENT DOCUMENTS

| DE | 10 2010 020 262 A1 | 11/2011 |
|---|---|---|
| EP | 0363654 A2 | 4/1990 |

(Continued)

OTHER PUBLICATIONS

Iceross. Instructions for use. www.ossur.com. Copyright 2010.*

(Continued)

*Primary Examiner* — Thomas J Sweet
*Assistant Examiner* — Christie Bahena
(74) *Attorney, Agent, or Firm* — Workman Nydegger

(57) ABSTRACT

A prosthetic socket system includes a socket having an inner surface defining a socket cavity. A liner is adapted to receive a residual limb and be removably positioned within the socket cavity. A substantially sealed volume is defined between at least a portion of an outer surface of the liner and a corresponding portion of the inner surface of the socket. A wicking material is positionable in the substantially sealed volume and at least one cooling fluid can be carried by the wicking material. The at least one cooling fluid is adapted to selectively boil within the substantially sealed volume such that heat from the residual limb is converted into latent heat of vaporization by the at least one cooling fluid for a cooling effect.

16 Claims, 7 Drawing Sheets

(51) Int. Cl.
*A61F 7/00* (2006.01)
*A61F 7/02* (2006.01)

(52) U.S. Cl.
CPC ... *A61F 2002/802* (2013.01); *A61F 2002/805* (2013.01); *A61F 2007/0051* (2013.01); *A61F 2007/0068* (2013.01); *A61F 2007/0069* (2013.01); *A61F 2007/0086* (2013.01); *A61F 2007/0093* (2013.01); *A61F 2007/0239* (2013.01)

(58) Field of Classification Search
CPC ............... A61F 2007/0292; A61F 7/02; A61F 2007/0239; A61F 2007/0069
See application file for complete search history.

(56) References Cited

U.S. PATENT DOCUMENTS

| | | | |
|---|---|---|---|
| 4,869,250 A * | 9/1989 | Bitterly | A41D 13/0053 607/107 |
| 5,885,509 A | 3/1999 | Kristinsson | |
| 6,010,528 A * | 1/2000 | Augustine | A61F 2/7843 297/452.21 |
| 6,136,039 A | 10/2000 | Kristinsson et al. | |
| 6,485,776 B2 | 11/2002 | Janusson et al. | |
| 6,626,852 B2 | 9/2003 | Janusson et al. | |
| 6,706,364 B2 | 3/2004 | Janusson et al. | |
| 7,001,563 B2 | 2/2006 | Janusson et al. | |
| 7,105,122 B2 | 9/2006 | Karason | |
| 7,118,602 B2 | 10/2006 | Bjarnason | |
| 8,052,760 B2 | 11/2011 | Egilsson et al. | |
| 8,097,043 B2 | 1/2012 | Egilsson | |
| 8,182,547 B2 | 5/2012 | King | |
| 8,308,817 B2 | 11/2012 | Egilsson et al. | |
| 8,475,537 B2 | 7/2013 | King | |
| 9,155,636 B1 | 10/2015 | Fikes | |
| 2001/0016781 A1 | 8/2001 | Caspers | |
| 2003/0109908 A1 | 6/2003 | Lachenbruch et al. | |
| 2004/0122528 A1 | 6/2004 | Egilsson | |
| 2007/0055383 A1 | 3/2007 | King | |
| 2007/0213839 A1 * | 9/2007 | Nachbar | A61F 2/60 623/26 |
| 2008/0221705 A1 * | 9/2008 | Scussel | A61F 2/80 623/32 |
| 2010/0125342 A1 * | 5/2010 | King | A61F 2/68 623/34 |
| 2010/0185300 A1 | 7/2010 | Mackenzie | |
| 2010/0274364 A1 * | 10/2010 | Pacanowsky | A61F 2/60 623/36 |
| 2011/0071649 A1 * | 3/2011 | McKinney | A61F 2/7812 623/34 |
| 2011/0282466 A1 | 11/2011 | Laghi | |
| 2012/0191217 A1 | 7/2012 | Mackenzie | |
| 2013/0025315 A1 * | 1/2013 | Freeman | F28D 15/0241 62/259.3 |
| 2013/0103125 A1 * | 4/2013 | Radspieler | A61F 7/02 607/104 |
| 2014/0025183 A1 | 1/2014 | Kelley et al. | |
| 2014/0379097 A1 | 12/2014 | Hurley et al. | |
| 2016/0081822 A1 * | 3/2016 | Zhe | A61F 2/80 623/33 |

FOREIGN PATENT DOCUMENTS

| | | |
|---|---|---|
| EP | 1875881 A1 | 1/2008 |
| WO | 2014/182767 A1 | 11/2014 |

OTHER PUBLICATIONS

O&PEdge. Prototype prosthetic cooling system wins UTSA entrepreneurship competition. May 3, 2013.*
International Search Report from International Application No. PCT/US2015/017026, dated May 8, 2015.
International Search Report from PCT Application No. PCT/US2016/048532, dated Oct. 26, 2016.

* cited by examiner

PROSTHETIC SOCKET SYSTEM

TECHNICAL FIELD

The disclosure relates to a prosthetic socket system for heat and perspiration management.

BACKGROUND

Prosthetic liners made of solid elastomer like silicone, copolymer gel, or polyurethane have been commercially available and used for a number of years as the media next to the skin in the majority of lower extremity prostheses.

Such liners have solved many issues like friction and pressure distribution; however, it has been difficult to achieve effective heat and sweat management when using a non-porous interface. For instance, moisture (e.g. sweat or condensation) within the liner can adversely affect limb health. Moisture decreases the friction suspending the liner on the residual limb. This can cause a pistoning action, which describes the relative movement between the liner and the residual limb.

Excessive limb pistoning tends to lead to friction-related injuries such as friction blisters and skin irritation. It also creates the potential for catastrophic failure of the suspension of the limb. Problems such as dermatitis and infection are also common, particularly if the liner and residual limb are not cleaned appropriately or frequently.

Attempts have been made to incorporate elements such as drain systems, heat exchangers, and semiconductors into known liners and/or prostheses to more effectively remove heat and sweat from the liner interface, yet, such designs are relatively complex, bulky, costly, and inevitably prohibit their use with a large majority of users.

To prevent such problems and to maintain secure adherence, users or amputees are currently required to manage the build-up of sweat in the liner themselves. They regularly have to remove their prosthesis to empty accumulated sweat and dry their limb.

There is thus a need for a prosthetic socket system that provides simple, comfortable, and effective heat and moisture management without removal of components of the system.

SUMMARY

The disclosure describes various embodiments of a prosthetic socket system providing simple, comfortable, and effective heat management, without the bulk and complexity of conventional heat management elements in known prosthetic socket systems. The embodiments can manage the build-up of sweat in a liner with heat management features that are easily and conveniently maintained, adjusted, and/or controlled without having to remove components from a user's prosthetic socket system.

The embodiments described can include a prosthetic system having a socket with an inner surface defining a socket cavity. A liner is adapted to receive a residual limb therein and to be removably positioned within the socket cavity. A substantially sealed volume is defined between at least a portion of the outer surface of the liner and a corresponding portion of the inner surface of the socket. A wicking material can be positioned in the substantially sealed volume and at least one cooling fluid is carried by the wicking material.

The at least one cooling fluid is adapted to selectively boil within the substantially sealed volume such that heat from the residual limb is converted into latent heat of vaporization by the at least one cooling fluid, extracting the heat for a cooling effect. This reduces sweating of the limb and the likelihood of friction-related injuries and skin irritation. Furthermore, it does so without the need of expensive and costly heat removal and/or draining elements as in the prior art.

The boiling point of the at least one cooling fluid can be selected or controlled to be higher or lower than one or more different temperature limits within the substantially sealed volume. This can help maintain the temperature of at least the distal end of the residual limb within a desired range and/or control the timing and level of heat removal achieved by the at least one cooling fluid.

According to a variation, a pump is operatively connected to the substantially sealed volume via a first aperture defined in the socket. The pump can create an elevated vacuum environment in the substantially sealed volume. This advantageously exhausts gases or vapors from the substantially sealed volume, which, in turn, removes additional energy or pressure buildup (e.g. kinetic energy created by the release of gases or vapors from the boiling cooling fluid), enhancing the cooling effect of the system.

This elevated vacuum environment can also lower the saturation vapor pressure, lowering the boiling point of the at least one cooling fluid. The pump can thus vary the boiling point of the at least one cooling fluid to remove heat from the residual limb, producing a cooling effect for the user on demand or when it is needed most. The pump can also be used to regulate the temperature of the residual limb during physical activities.

According to a variation, the socket defines a second aperture in fluid communication with the substantially sealed volume. The second aperture can be coupled to a one-way valve that allows the at least one cooling fluid to be introduced into the substantially sealed volume. This advantageously allows the at least one cooling fluid to be supplied and/or replenished to the wicking material after the prosthetic socket system is positioned on the residual limb, without having to remove components from the system, making the system easier and more comfortable to use.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

These and other features, aspects, and advantages of the present disclosure will become better understood regarding the following description, appended claims, and accompanying drawings.

DETAILED DESCRIPTION OF VARIOUS EMBODIMENTS

Figure 1:
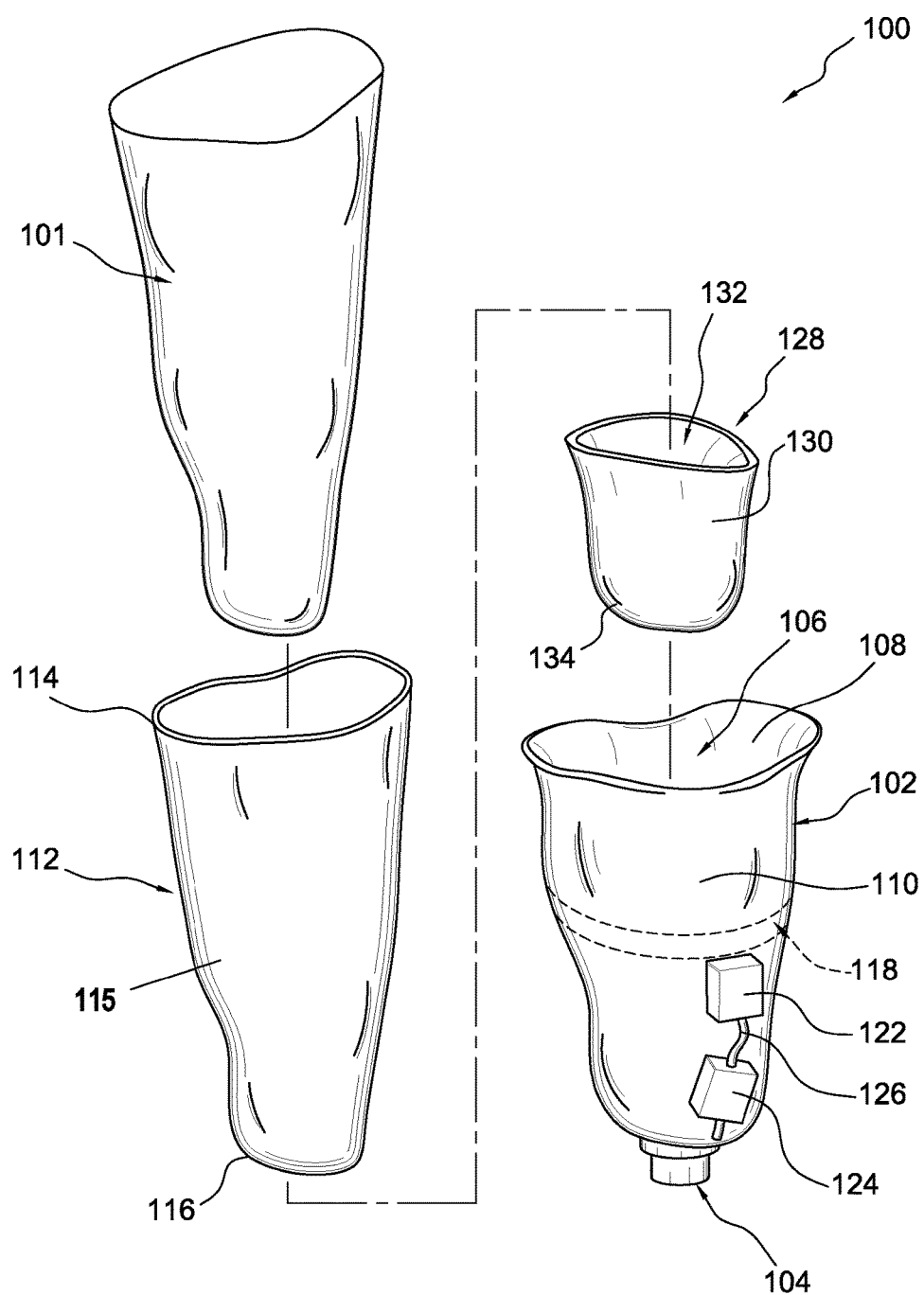
FIG. 1 is an exploded view of a prosthetic socket system according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the embodiments of an orthopedic device as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of elements that provide support and are free-standing; however, such elements may have some degree of flexibility or resiliency.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112, paragraph 6.

Figure 2:
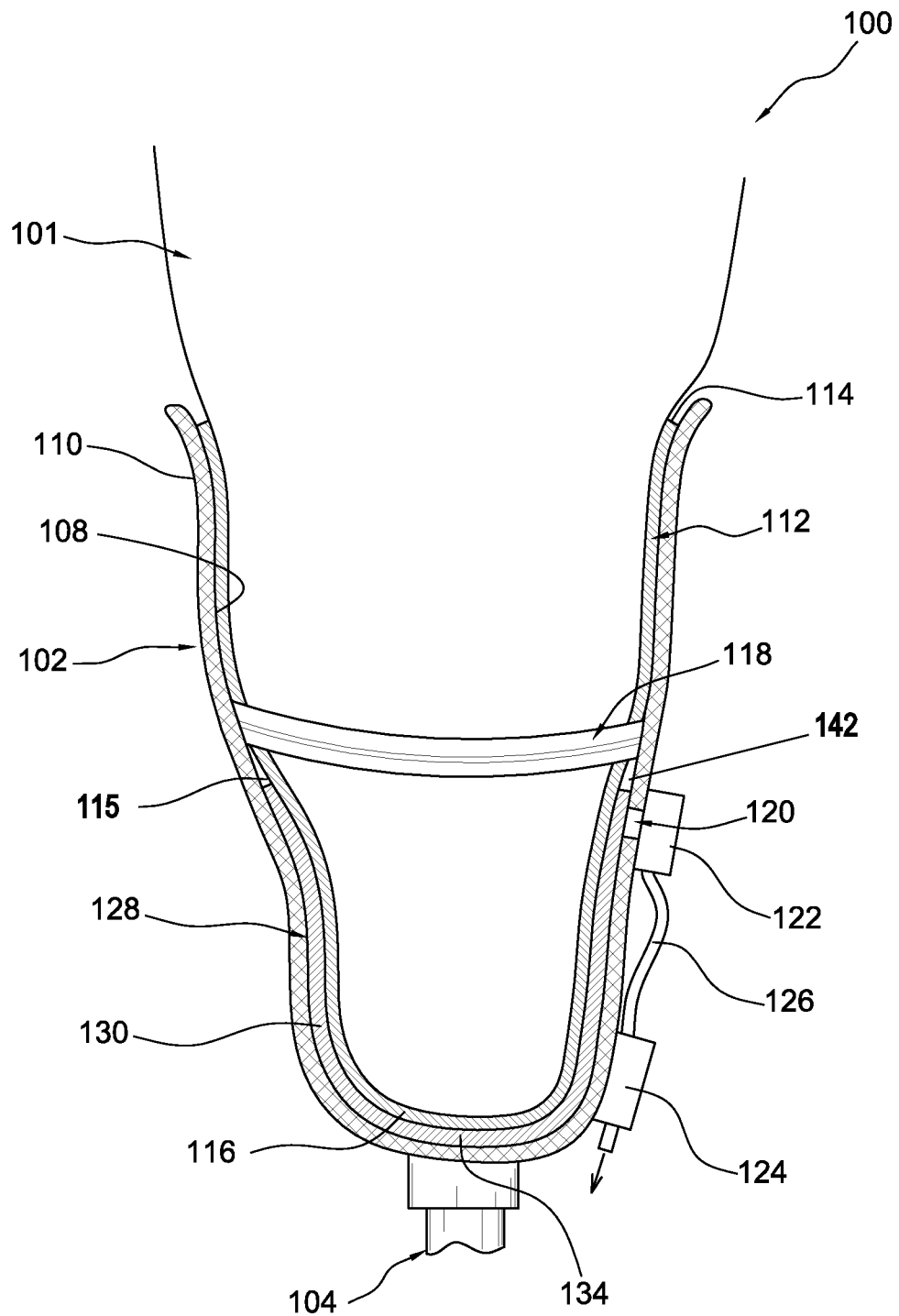
FIG. 2 is a cross-sectional view of the prosthetic socket system shown in FIG. 1 according to an embodiment.
Figure 3:
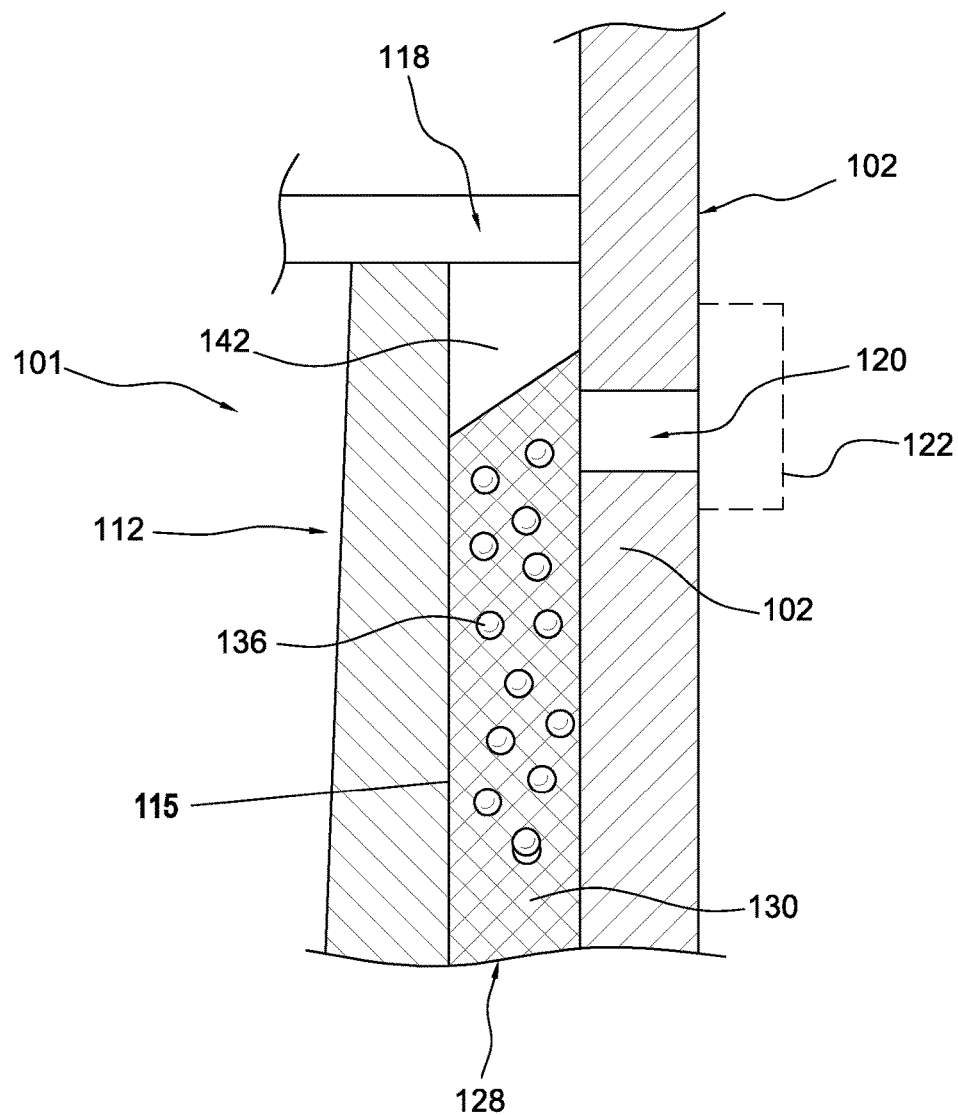
FIG. 3 is a detailed cross-sectional view of the prosthetic socket system according to an embodiment.

FIGS. 1-3 show a first embodiment of the prosthetic socket system comprising a prosthetic socket system 100. As seen in FIGS. 1 and 2, the system 100 includes a socket 102 having an outer surface 110 and an opposing inner surface 108 defining a socket cavity 106. The inner surface 108 is arranged as a close-ended cup with an open proximal end and a closed distal end area. The open proximal end of the inner surface 108 is adapted to receive a distal portion of the residual limb 101 to be located in the socket cavity 106.

A liner 112 is adapted to be removably positioned within the socket cavity 106 and to receive a residual limb 101 therein. The liner 112 can include a body that extends between a proximal end 114 and a distal end area 116 and can comprise an air-impermeable elastomeric material such as silicone, copolymer gel, polyurethane, urethane, thermoplastic elastomer, RTV rubber, combinations thereof, or any other appropriate material.

The liner 112 is typically donned on the residual limb 101 and the limb 101 and the liner 112 are then inserted in the socket cavity 106 of the socket 102. The softer elastomer of the liner 112 adheres to the skin of the residual limb 101 frictionally to thereby secure the residual limb 101 within the liner 112. The liner 112, on the other hand, remains contained within the socket cavity 106 after it has been fully inserted into the distal end area of the socket cavity 106 by creating a seal between the socket 102 and the liner 112.

A seal may refer to a component of the system 100 that allows a vacuum to be formed between the liner 112 and the socket 102. In the illustrated embodiment, a seal element 118 can be associated with the liner 112 to create a vacuum between the socket 102 and the liner 112. Any pulling forces applied to the liner 112 will result in a suction being created between the liner 112 and the socket 102.

A substantially sealed volume 142 can be defined distally of the seal element 118 and between at least a portion of the outer surface 115 of the liner 112 and a corresponding portion of the inner surface 108 of the socket 102, substantially isolating this area from atmosphere.

A wicking material 128 is positionable in the substantially sealed volume 142. As seen, the wicking material 128 can have a sock-like configuration including a generally continuous sidewall 130, an open top 132, and a closed bottom 134.

The wicking material 128 can be generally compressible, and selectively removable from the system 100. For example, the wicking material 128 can be selectively donned on the outer surface 115 of the liner 112. The wicking material 128 can be positioned on the liner 112 and then the liner 112 and the wicking material 128 can be inserted in the socket cavity 106 of the socket 102. This advantageously allows the wicking material 128 to be removed from the prosthetic socket system 100 for hygienic purposes, for replacement, for repair, or for any desired purpose.

Alternatively, the wicking material 128 can be removably attached to the socket cavity 106 of the socket 102. In other embodiments, the wicking material 128 can be bonded or fixedly attached to the liner 112 or the socket cavity 106.

The wicking material 128 can comprise one or more porous materials having one or more wicking properties. For example, the wicking material 128 can comprise a woven material, a perforated material, a sponge-like material, combinations thereof, or any other suitable material. The wicking material 128 can comprise polyester, wool, cotton, synthetic materials, natural materials, a sponge-like material, combinations thereof, or any other suitable material.

As seen in FIG. 3, at least one cooling fluid 136 can be supplied to the substantially sealed volume 142 and/or the wicking material 128 within the substantially sealed volume 142. The at least one cooling fluid 136 is arranged to remove energy/heat from the liner 112 and/or residual limb 101 by absorbing and/or converting such heat into other forms of energy for a cooling effect.

The at least one cooling fluid 136 can include water, deionized water, substantially pure water, an alcohol, a dielectric fluid, a solution, oil, a refrigerant, a glycol, a gel-like material, combinations thereof, or any other suitable fluid. The at least one cooling fluid 136 can include a single liquid or a solution or mixture of a plurality of liquids. The at least one cooling fluid 136 can include a mixture of liquids, vapor, and/or gases. The at least one cooling fluid 136 can be selected based on one or more physical and/or chemical properties. For example, the at least one cooling fluid may be selected based on boiling point, thermal conductivity, specific heat, viscosity, freezing point, flash point, corrosivity, toxicity, thermal stability, combinations thereof, or any other suitable property.

During use, the temperature of the residual limb 101 within the distal end area of the socket cavity 106 can increase until it becomes greater than the temperature of the outer surface 115 of the liner 112 wherein the wicking material 128 and the at least one cooling fluid 136 are located.

When the temperature of the residual limb 101 is greater than the at least one cooling fluid 136, heat/energy is transferred from the residual limb 101 through the liner 122 and to the at least one cooling fluid 136 until a thermal equilibrium is established, that is the residual limb 101, the liner 112, and the at least one cooling fluid 136 reach the same temperature. The direction of energy transfer is always from the higher temperature body to the lower temperature one. Thus, heat/energy is transferred from the higher temperature residual limb 101 to the lower temperature of the at least one cooling fluid 136, cooling the residual limb 101 and increasing the temperature of the at least one cooling fluid 136.

When the temperature of the at least one cooling fluid 136 reaches and/or exceeds its boiling point, the at least one cooling fluid 136 within the substantially sealed volume 142 begins to boil. More particularly, as the temperature of the at least one cooling fluid 136 increases, the energy transferred from the residual limb 101 is absorbed by the molecules of the at least one cooling fluid 136. This in turn causes the molecules to acquire additional kinetic energy and increases molecular motion (vibrations and molecules slipping past each other).

Eventually, when the temperature of the at least one cooling fluid 136 reaches and/or exceeds its boiling point, the molecular motion becomes so intense that the forces of attraction between the molecules are disrupted to the extent that at least some of the molecules break free from the at least one cooling fluid 136 in liquid form and become a gas or vapor which rises from the at least one cooling fluid 136.

The latent heat of vaporization is the amount of energy absorbed by the at least one cooling fluid 136 during this process of vaporization. For example, if the at least one cooling fluid 136 is pure water, and at 1 atm pressure, the cooling fluid 136 can absorb and/or remove about 2200 Joules (0.52 calories) from the residual limb 101 with each gram of boiled water. The boiling point of at least one cooling fluid 136 can be selected to be lower than a first temperature limit associated with the substantially sealed volume 142, the distal end of the residual limb 101, and/or the liner interface between the residual limb 101 and the liner 112 in the area of the substantially sealed volume 142, activating the system 100 or helping to prevent the residual limb 101 from overheating. The boiling point of at least one cooling fluid 136 can be selected to be higher than a second temperature limit associated with the substantially sealed volume 142, the distal end of the residual limb 101, and/or the liner interface between the residual limb 101 and the liner 112 in the area of the substantially sealed volume 142, helping to prevent the residual limb 101 from becoming too cold or deactivating the system 100.

The system can thus advantageously extract heat from the residual limb 101 at least in part through the conversion of such heat to latent heat of vaporization, providing the user a cooler more comfortable fit, which, in turn, reduces sweating of the residual limb 101 and the likelihood of friction-related injuries and skin irritation. Furthermore, it does so without the need of expensive and costly heat removal or drainage elements.

To permit expulsion of the gases or vapors rising from the boiling cooling fluid 136 and/or purging of other fluids from the substantially sealed volume 142, an aperture 120 can be defined by the socket 102 that extends through the inner surface 108 and the outer surface 110 of the socket 102. The substantially sealed volume 142 can be in fluid communication with atmosphere external to the socket 102 via the aperture 120. A valve 122 may be provided separately or integrally with the aperture 120. The valve 122 can be a one-way valve that selectively permits fluids to flow from the substantially sealed volume 142 through the aperture 120 to atmosphere external to the socket 102, but not in the other direction.

It will be appreciated that by exhausting the gases or vapors from the substantially sealed volume 142, additional heat or energy can be removed from the residual limb or interface of the residual limb 101 and the liner 112 by relieving pressure buildup (e.g. kinetic energy created by the release of the gases or vapors) within the substantially sealed volume 142.

Optionally, a pump 124 (shown in FIGS. 1 and 2) may be in fluid communication with the substantially sealed volume 142 via the aperture 120. The pump 124 can create an elevated vacuum environment in the substantially sealed volume 142. This can beneficially enhance the purging or exhaustion of fluids from the substantially sealed volume 142. It can also increase the effectiveness of the system 100 in removing heat or energy from residual limb 101 or the liner interface between the residual limb 101 and the liner 112. The pump 124 may comprise a manual, an electric pump, a wet/dry pump, or any other suitable pump.

For instance, an elevated vacuum environment in the substantially sealed volume 142, by lowering saturation vapor pressure, lowers the boiling point of the at least one cooling fluid 136. The pump 124 can thus vary the boiling point of the at least one cooling fluid 136. As such, the pump 124 can be operated to create an elevated vacuum level within the substantially sealed volume 142 that lowers the boiling point of the at least one cooling fluid 136 below the ambient or surrounding temperature within the substantially sealed volume 142, which, in turn, will cause the at least one cooling fluid 136 to boil. The boiling point of at least one cooling fluid 136 can be controlled (or selected) to be lower or higher than one or more temperature limits associated with the substantially sealed volume 142, the distal end of the residual limb 101, and/or the liner interface between the residual limb 101 and the liner 112 in the area of the substantially sealed volume 142. This can help maintain the temperature of the residual limb 101 within a desired range and/or control the timing and/or level of heat removal achieved by the at least one cooling fluid 136.

As discussed above, as the at least one cooling fluid 136 boils, it removes or absorbs heat from its surroundings (e.g., the residual limb 101 and the liner 112) by converting such heat into latent heat of vaporization. Operation of the pump 124 can thus advantageously produce a cooling effect for the user on demand or when it is needed most. The pump 124 can also be advantageously used to regulate the temperature of the residual limb 101 during physical activities such as walking or sports.

Further, with a substantially constant flow of heat or energy from the residual limb 101 and/or the liner 112 towards the at least one cooling fluid and removal of the vapors or gases from the substantially sealed volume 142 at the same time by the pump 124, the at least one cooling fluid 136 can keep boiling and thereby keep removing heat or energy from the residual limb 101 until the at least one cooling fluid 136 is boiled away. This can advantageously transfer heat or energy away from the residual limb 101 in a generally continuous flow without the insulating effect of the socket 102 playing a significant role.

The pump 124 can be operated to create an elevated vacuum level that moves the boiling point of the at least one cooling fluid 136 to a target boiling point that is selected to help maintain the temperature of at least the distal end of the residual limb 101 in the socket cavity 106 below a desired temperature.

It will be appreciated that the elevated vacuum environment generated by the pump 124 can also increase the suction created between the distal end area 116 of the liner 112 and the corresponding inner surface 108 of the socket.

The elevated vacuum level or elevated vacuum environment established by the pump 124 may be selected based on characteristics of the user, the at least one cooling fluid 136, and/or other factors. The pump 124 can pull a continuous or a non-continuous vacuum in the substantially sealed volume 142. For instance, the system 100 can include a controller arranged to direct the pump 124 to establish the elevated vacuum environment in the substantially sealed volume 142 based on feedback from at least one pressure or temperature sensor.

Referring again to FIGS. 1 and 2, the pump 124 can be attached to the socket 102. The pump 124 can be separate from the socket 102. The pump 124 is arranged to be operated by the user's gait. For instance, the pump 124 can be connected to a prosthetic foot and include a conduit in fluid communication with the aperture 120. The pump 124 is arranged to pull a vacuum in the substantially sealed volume 142 in step phase, and to expel gases or vapors and associated pressure into the atmosphere in swing phase.

The pump 124 can thus utilize the motion of the prosthetic foot to boil the at least one cooling fluid 136 and remove heat or energy from the residual limb 101 or the interface between the residual limb 101 and the liner 112, for a cooling effect. Cooling occurs when the user is ambulating. This is advantageous because warming up and sweating of the residual limb 101 rarely occurs unless some activity is occurring. Other examples of suitable gait actuated pumps are found in U.S. patent application Ser. Nos. 13/873,394 and 13/873,315, which are incorporated herein by reference in their entirety.

The one-way valve 122 can be integral to the pump 124. The pump 124 can be fluidly connected to the one-way valve 122 via a tube 126. Hoses, fittings, or other connection mechanisms may be situated between the pump 124, the one-way valve 122, and/or the aperture 120. The valve 122 can have any suitable construction and may take the form of an electronic valve, a duck-billed valve, a slit valve, a spring biased element check valve, or any other suitable type of valve. The valve 122 can be selected for use based upon an actuation pressure. The valve 122 can be a two-way valve actuated by a controller, the pump 124, pressure differential, or another trigger. The pump 124 can supply the at least one cooling fluid 136 to the substantially sealed volume 142 via the aperture 120 and the valve 122 when the valve 122 is a two-way valve.

The wicking material 128 includes a cross-sectional area and surface area that can carry, pick up, and/or distribute the at least one cooling fluid 136, facilitating boiling of the at least one cooling fluid 136.

The wicking material 128 can include one or a plurality of layers. For instance, the wicking material 128 can include a first layer and a second layer spaced from the first layer. A region can be defined between the first and second layers. The at least one cooling fluid 136 can be disposed within the region of the wicking material 128 and the pores of the wicking material 128 can be in fluid communication with the region.

The wicking material 128 can have any suitable configuration but is described having a sock-like configuration. For instance, the wicking material 128 has an open-ended sleeve configuration. The wicking material 128 can be an elongate strip of material arranged to be wrapped around the liner 112. The wall 130 of the wicking material 128 can be continuous.

The wall 130 of the wicking material 128 can be non-continuous (e.g. including one or more openings or slots defined therein. The wall 130 of the wicking material 128 can include a plurality of strips that are spaced apart and extending between a rim defining the open top 132 and the closed bottom 134 of the wicking material 128.

The wicking material 138 can substantially fill all or a portion of the substantially sealed volume 136. The wicking material 138 can extend through some or all of a gap defined between the inner surface 108 of the socket 102 and the outer surface 115 of the liner 112. Alternatively, the wicking material 128 can be omitted. For instance, the at least one cooling fluid 136 can be supplied directly to the substantially sealed volume without the wicking material 128.

The at least one cooling fluid 136 can be supplied to the wicking material 128 via any suitable technique. The wicking material 128 can be wetted with the at least one cooling fluid 136 before positioning the wicking material 128 in the substantially sealed volume 142. The at least one cooling fluid 136 can be sprayed onto the wicking material 128. The at least one cooling fluid 136 can be supplied to the wicking material 128 via the aperture 120 or another port defined in the socket 102.

Alternatively, the at least one cooling fluid 136 can be located within a plurality of beads, particles, or fibers attached and/or carried by the wicking material 128. For instance, the beads can be arranged to burst when a target temperature is reached or when they are squeezed between the liner 112 and the inner surface 108 of the socket 102.

The at least one cooling fluid 136 can include different cooling fluids arranged for different activities and/or conditions. For instance, the at least one cooling fluid 136 can include a cooling fluid adapted for sporting activities. The at least one cooling fluid 136 can include a cooling fluid adapted for winter or summer type conditions.

It will be appreciated that while one aperture 120 is described in the sidewall of the socket 102, in other embodiments, any suitable number of apertures may be located in any suitable manner within the socket cavity 106. For example, a plurality of apertures may be provided axially and circumferentially spaced along the socket cavity 106. In other embodiments, the aperture 120 may be formed through the distal end of the socket.

The seal element 118 can have any suitable configuration. For example, the seal element 118 may be tapered outwardly from its distal end towards its proximal end to facilitate insertion of the liner 112 into the socket cavity 106 and tends to resist outward movement of the liner 112 from the socket cavity 106 of the socket 102.

Also, the form of the seal element 118 can provide an increased sealing force between the liner 112 and the socket 102 when the liner 112 is moved in a direction towards the distal end of the liner 112 when subjected to a pressure differential where a lower pressure exists towards the distal side of the seal as compared to the proximal side thereof. Other examples of suitable seal elements are found in U.S. Pat. Nos. 8,308,817; 8,097,043; 8,052,760; 8,034,120; 8,372,159; 8,372,159; and 8,894,719, and U.S. patent application Ser. Nos. 13/589,415; 13/748,891; 13/765,127; 13/826,748; 14/187,681; 14/203,715; and 14/281,424, each of which are incorporated herein by reference in their entirety.

In other embodiments, the inner surface of the socket 102 can include an annular seal or flange secured thereto or the seal element may be omitted.

The liner 112 can be soft and at least radially distensible elastically. The liner 112 may also be elastically distensible axially or may have limited axial elasticity. The liner 112 may be thickened to provide a cushioning effect between the residual limb 101 and the socket 102 and may be used for both trans-tibial (TT) amputees as well as trans-femoral (TF) amputees. That is, the liner 112 may be utilized for applications above the knee or below the knee of the amputee. Exemplary liners are found in U.S. Pat. Nos. 6,136,039; 6,626,952; 6,485,776; 6,706,364; 7,001,563; and 7,118,602, each of which are incorporated herein by reference in their entirety.

The socket 102 can exhibit any suitable configuration. The socket 102 can be constructed of any suitable materials. The socket 102 can be cast, molded, laminated, or otherwise formed of synthetic and/or reinforced components. The socket 102 is described having a unitary construction forming a shell but can include an assembly of a plurality of components. An example of a suitable socket is found in U.S. Pat. Nos. 5,885,509 and 7,105,122, which are incorporated herein in their entirety by reference.

The socket 102 can be structurally rigid, structural, load-bearing, and can provide a user with the security as expected under normal usage conditions as the volume of the socket 102 will not change under a load. The socket cavity 106 may have a generally cylindrical or conical shape. Alternatively, the socket cavity 106 can have a customized shape that substantially corresponds to the general shape of the residual limb of a particular user.

The socket 102 is preferably air impervious. The socket 102 may have a socket adapter 104 located at the distal portion of the socket shell 102 for connecting the socket 102 to a prosthetic limb (not shown) such as a prosthetic knee, ankle, or elbow joint. The adapter 104 may be any suitable conventional adapter, such as a pyramid connection or a threaded connection.

Figure 4:
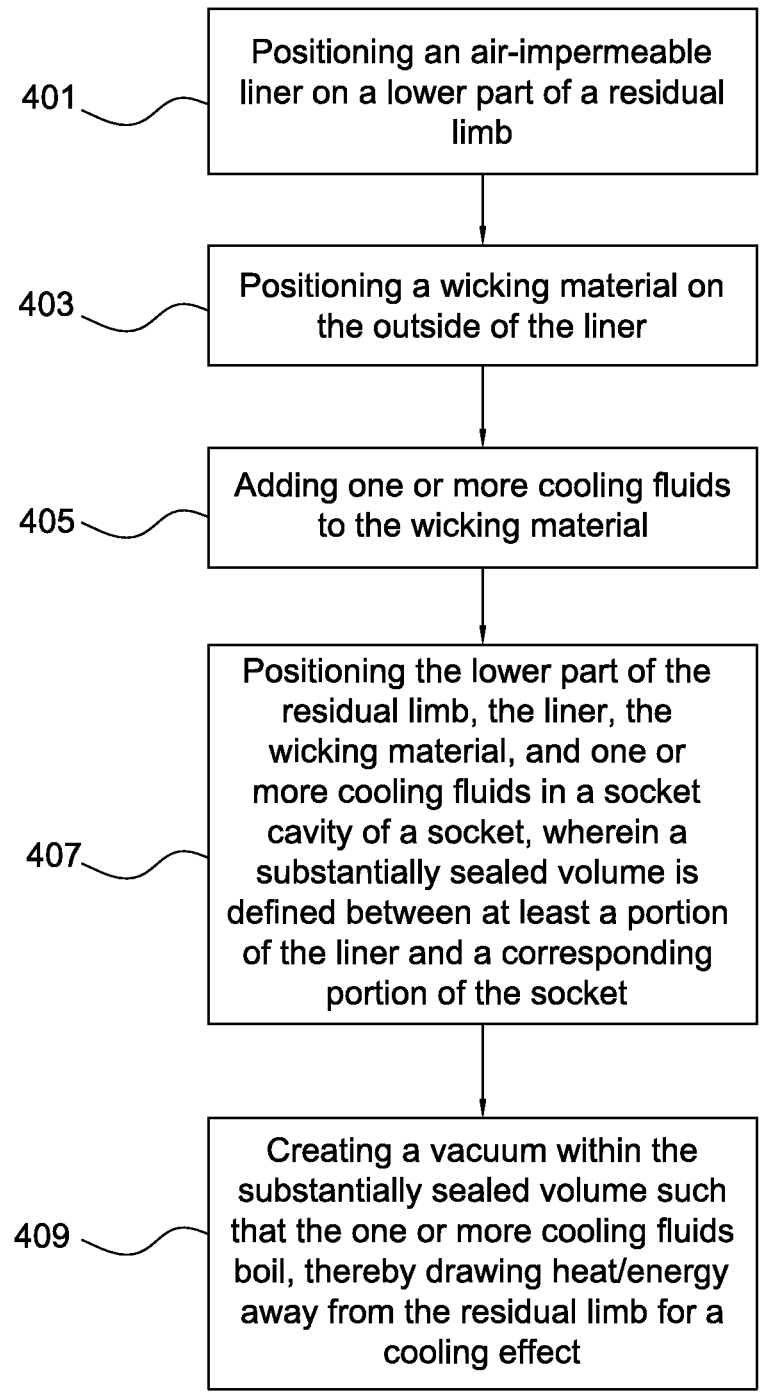
FIG. 4 illustrates a method for utilizing a prosthetic socket system according to an embodiment.

A method of using the prosthetic socket system 100 according to an embodiment will now be described in relation to FIG. 4. The method 400 includes a step 401 of positioning an air-impermeable liner on a lower part of the residual limb. With the liner positioned on the residual limb, the method 400 includes a step 403 of positioning the wicking material on the outside of the liner. The method 400 includes a step 405 of adding or supplying (e.g., wetting, spraying, soaking, etc.) one or more cooling fluids to the wicking material. The wicking material can be wetted with the cooling fluids before or after the wicking material is positioned on the liner.

The method 400 includes a step 407 of positioning the lower part of the residual limb, the liner, and the wetted wicking material in the socket cavity of the socket. The wicking material is positioned in a substantially sealed volume defined between at least a portion of the liner and a corresponding portion of the socket. Finally, the method 400 includes a step 409 of creating a vacuum within the substantially sealed volume such that the one or more cooling fluids boil, thereby drawing heat/energy away from the residual limb for a cooling effect.

In an alternative embodiment, the wicking material can be omitted. For example, the one or more cooling fluids can be supplied between the liner and the socket without the wicking material.

Figure 5:
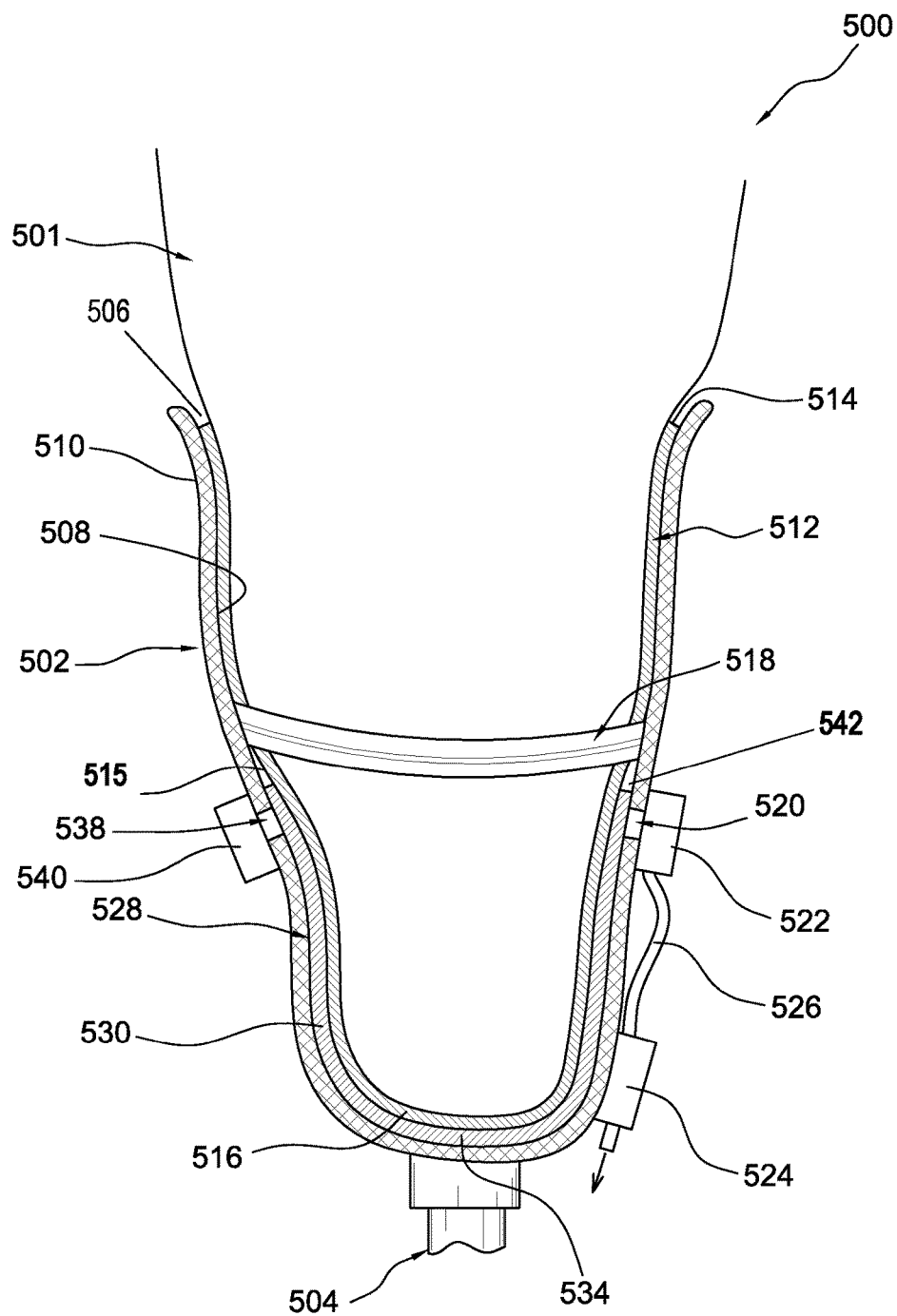
FIG. 5 is a cross-sectional view of a prosthetic socket system according to another embodiment.

Another exemplary embodiment of a prosthetic socket system 500 is shown in FIG. 5. This embodiment is similar to system 100 except that the socket 502 includes a second aperture 538 in communication with a substantially sealed volume 542. The socket 502 has an outer surface 510 and an inner surface 508 defining a socket cavity 506. A socket adaptor 504 located at the distal end of the socket 502 for connecting the socket 502 to a prosthetic limb.

A liner 512 is adapted to be removably positioned within the socket cavity 506 and to receive a residual limb 501 therein. The liner 512 can include a body that extends between a proximal end 514 and a distal end area 516.

The substantially sealed volume 542 is defined between at least a portion of the outer surface 515 of the liner 512 and a corresponding portion of the inner surface 508 of the socket 502. In the illustrated embodiment, a seal element 518 is associated with the liner 512 that at least in part defines the substantially sealed volume 542.

Similar to the previously described embodiments, a wicking material 528 and/or at least one cooling fluid are positionable in the substantially sealed volume 542. The wicking material 528 has a sidewall 530, an open top, and a closed bottom 534. The at least one cooling fluid is arranged to selectively boil within the substantially sealed volume 542 such that heat from the residual limb 501 is converted into latent heat of vaporization, extracting the heat from the residual limb for a cooling effect. This advantageously reduces sweating of the limb and the likelihood of friction-related injuries and skin irritation. Furthermore, it does so without the need of expensive and costly heat removal and/or draining elements.

A first aperture 520 is defined in the socket 502 that extends through the inner surface 508 and the outer surface 510 of the socket 502. The substantially sealed volume 542 can be in fluid communication with the atmosphere external to the socket 102 via the first aperture 520. A first one-way valve 522 selectively allows fluids to be expelled from the substantially sealed volume 542 through the first aperture 520 to atmosphere, but not in the other direction.

A pump 524 can be fluidly connected to the first one-way valve 522 via a tube 526. The pump 524 can be arranged to create an elevated vacuum environment in the substantially sealed volume 542. This can beneficially enhance the purging or exhaustion of fluids from the substantially sealed volume 542. It can also increase the effectiveness of the system 500 in removing heat or energy from residual limb 501 or the liner interface between the residual limb 501 and the liner 512.

The second aperture 538 is also defined through the inner and outer surfaces 508, 510 of the socket 502. The second aperture 538 can be coupled to a second valve 540 adapted to at least allow the at least one cooling fluid to be supplied and/or replenished within the substantially sealed volume 542. This advantageously allows the at least one cooling fluid to be supplied and/or replenished to the wicking material after the prosthetic socket system 500 is positioned on the residual limb, without having to remove components from the system 500, making the system 500 easier and more comfortable to use. The second valve 540 can be a one-way valve or a two-way valve.

Figure 6:
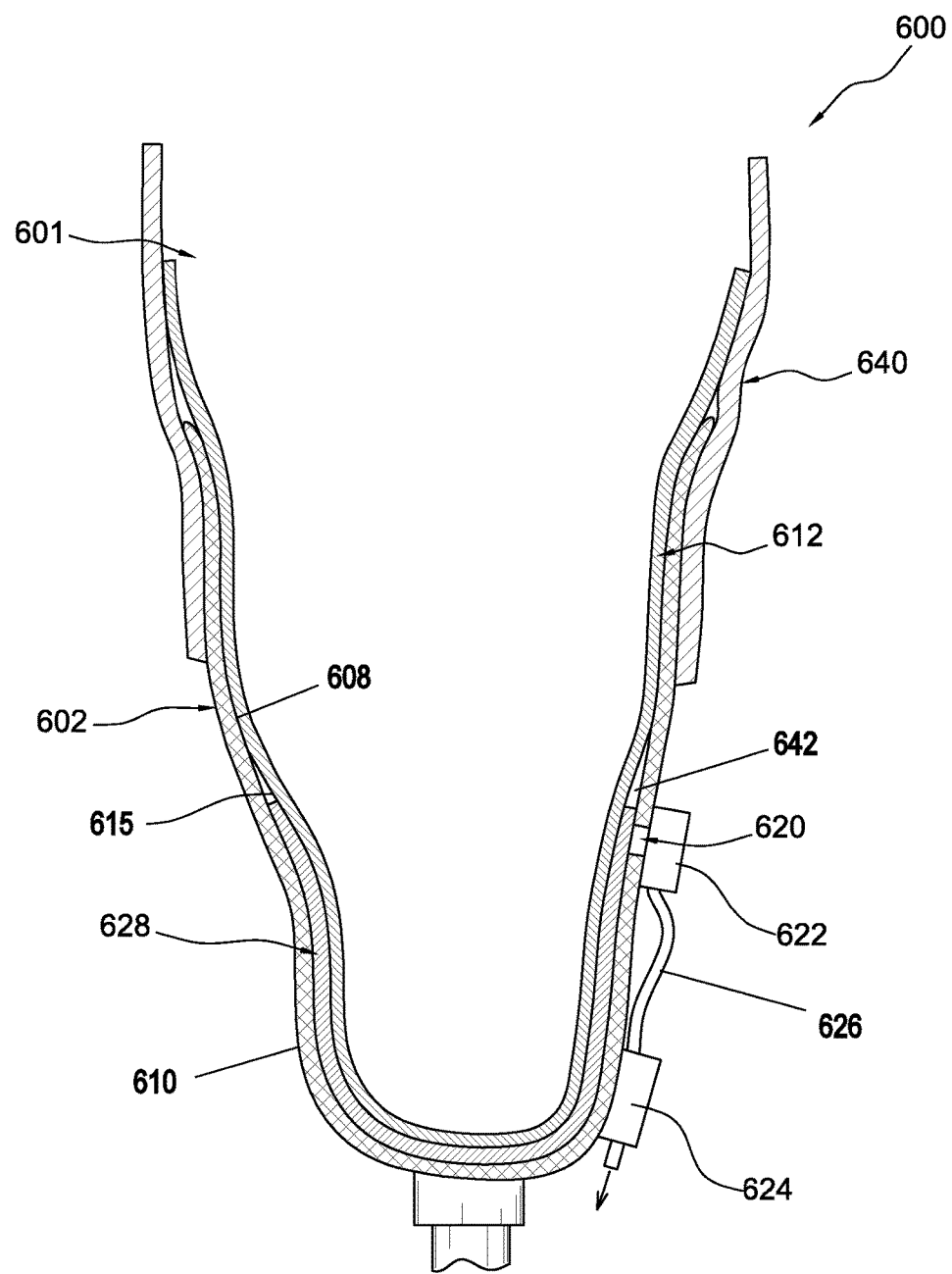
FIG. 6 is a cross-sectional view of a prosthetic socket system according to another embodiment.

Another exemplary embodiment of a prosthetic socket system 600 is shown in FIG. 6. This embodiment is similar to the embodiment of FIGS. 1-3 except that there is no seal element associated with the liner 612. As seen, a socket 602 includes an inner surface 608 defining a socket cavity and a liner 612 is adapted to be removably positioned within the socket cavity of the socket 602. The liner 612 is adapted to receive a residual limb 601 therein.

A prosthetic sleeve 640 is positioned on the residual limb 601 and an outer surface 610 of the socket 602. The prosthetic sleeve 640 can create a seal between the proximal end of the socket 602 and the liner 612, as disclosed in U.S. Pat. No. 8,097,043, incorporated by reference in its entirety. A portion of the prosthetic sleeve 640 can be rolled over the brim of the socket 602. An example of a suitable prosthetic sleeve is found in U.S. Pat. No. 6,592,539, the entirety of which is incorporated herein by reference.

The substantially sealed volume 642 can be defined between at least the seal formed by the prosthetic sleeve 640, the outer surface 615 of the liner 612, and the inner surface 608 of the socket 602. Similar to the system 100, a wicking material 628 and/or at least one cooling fluid are positionable in the substantially sealed volume 642. The at least one cooling fluid is arranged to selectively boil within the substantially sealed volume 642 such that heat from the residual limb 601 is converted into latent heat of vaporization.

An aperture 620 is defined in the socket 602 that extends through the inner surface 608 and the outer surface 610 of the socket 602. The substantially sealed volume 642 can be in fluid communication with the atmosphere external to the socket 602 via the aperture 620. A one-way valve 622 selectively allows fluids to be expelled from the substantially sealed volume 642 through the aperture 620 to atmosphere, but not in the other direction. A pump 624 can be fluidly connected to the one-way valve 622 via a tube 626. The pump 624 can be arranged to create an elevated vacuum environment in the substantially sealed volume 642. This can beneficially enhance the purging or exhaustion of fluids from the substantially sealed volume 642. It can also increase the effectiveness of the system 600 in removing heat or energy from residual limb 601 or the liner interface between the residual limb 601 and the liner 612.

Figure 7:
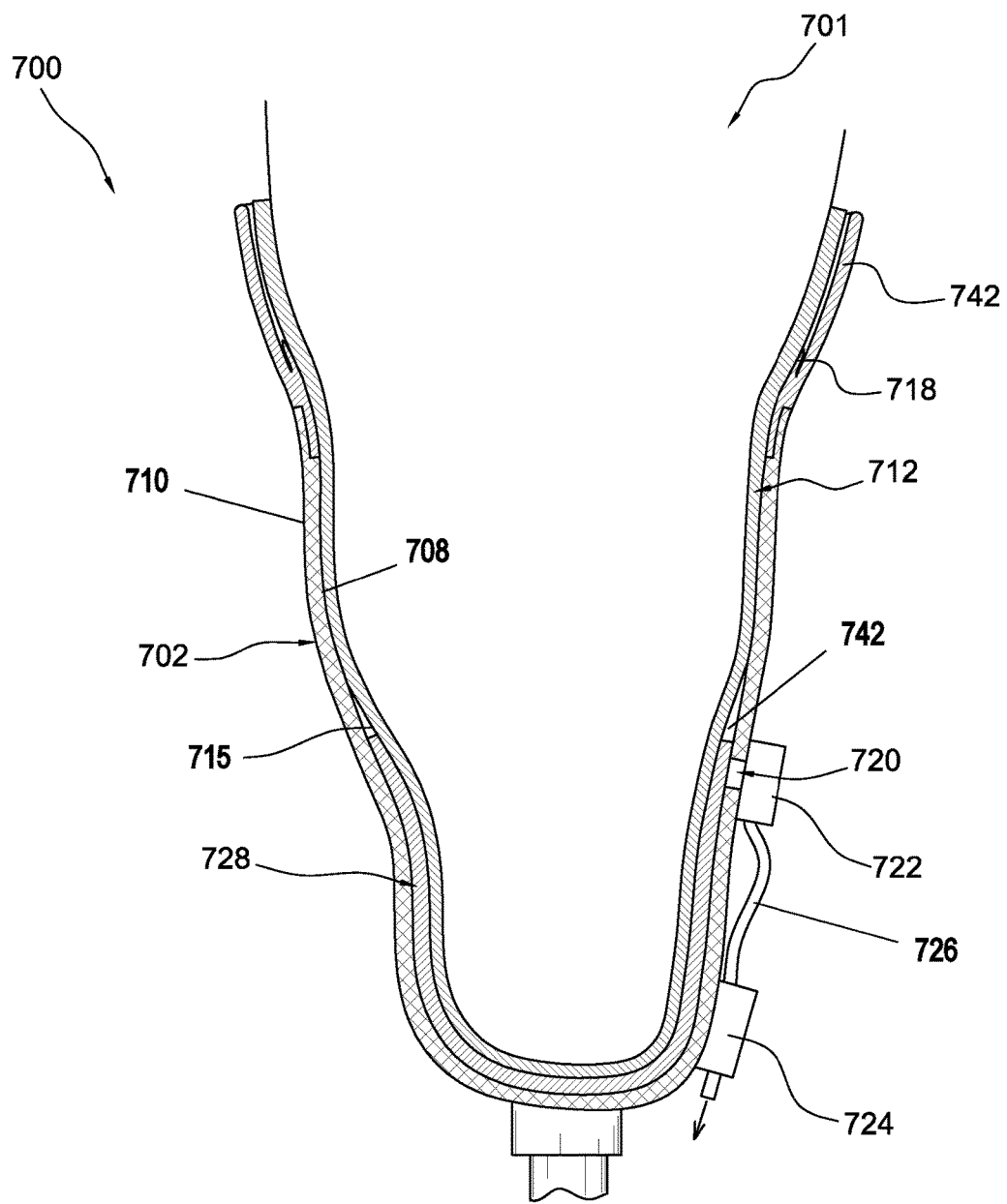
FIG. 7 is a cross-sectional view of a prosthetic socket system according to another embodiment.

Another exemplary embodiment of a prosthetic socket system 700 is shown in FIG. 7. This embodiment is similar to the embodiment of FIGS. 1-3 except that the seal element 718 is associated with the liner 712. A socket 702 includes an inner surface 708 defining a socket cavity and a liner 712 is adapted to be removably positioned within the socket cavity of the socket 702. The liner 712 is adapted to receive a residual limb 701 therein.

The socket 702 includes a flexible brim 742 defining a seal element 718 arranged to form a seal between the liner 712 and the proximal end of the socket 702. An example of a suitable seal element on a socket is found in U.S. patent application Ser. No. 14/457,379, the entirety of which is incorporated herein by reference.

As seen, the substantially sealed volume 742 can be defined between the seal element 718 on the socket 702, the outer surface 715 of the liner 712, and the inner surface 708 of the socket 702. Similar to the previously described systems, a wicking material 728 and/or at least one cooling fluid are positionable in the substantially sealed volume 742. The at least one cooling fluid is arranged to selectively boil within the substantially sealed volume 742 such that heat from the residual limb 701 is converted into latent heat of vaporization for a cooling effect.

An aperture 720 is defined in the socket 702 that extends through the inner surface 708 and the outer surface 710 of the socket 702. The substantially sealed volume 742 can be in fluid communication with the atmosphere external to the socket 702 via the aperture 720. A one-way valve 722 selectively allows fluids to be expelled from the substantially sealed volume 742 through the aperture 720 to atmosphere, but not in the other direction. A pump 724 can be fluidly connected to the one-way valve 722 via a tube 726. The pump 724 can be arranged to create an elevated vacuum environment in the substantially sealed volume 742.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

What is claimed is:

1. A prosthetic socket system comprising:
    a prosthetic socket including a sidewall, first and second apertures formed in the sidewall and an inner surface defining a socket cavity;
    a liner adapted to receive a residual limb of a user therein and to be removably positioned within the socket cavity;
    a seal element located between the liner and the inner surface of the socket, the seal element defining a substantially sealed volume between at least a portion of the liner and a corresponding portion of the inner surface of the socket;
    a wicking material separate from the liner and positioned in the substantially sealed volume, the wicking material soaked with a supply of at least one cooling fluid sized and configured such that the at least one cooling fluid is available for boiling within the substantially sealed volume when a temperature of the residual limb exceeds a temperature of the at least one cooling fluid during physical activity of the user, the wicking material repeatedly installable on the outer surface of the liner and the at least one cooling fluid adapted to selectively boil within the substantially sealed volume such that heat from the residual limb is converted into latent heat of vaporization by the at least one cooling fluid for a cooling effect, wherein the second aperture is arranged in communication with an external supply of the at least one cooling fluid, for delivering the at least one cooling fluid to the wicking material within the substantially sealed volume; and
    a pump operatively connected to the substantially sealed volume via the first aperture, the pump arranged to selectively create an elevated vacuum in the substantially sealed volume.

2. The system of claim 1, wherein the at least one cooling fluid comprises an alcohol.

3. The system of claim 1, wherein the elevated vacuum created by the pump lowers a boiling temperature of the at least one cooling fluid below an ambient temperature in the substantially sealed volume.

4. The system of claim 1, wherein the elevated vacuum created by the pump is dependent on one or more characteristics of the user.

5. The system of claim 1, wherein the pump is arranged to exhaust gases rising from the at least one cooling fluid from the substantially sealed volume.

6. The system of claim 1, further comprising a one-way valve fluidly connected with the first aperture.

7. The system of claim 1, wherein the seal element is formed on the liner.

8. The system of claim 1, wherein the seal element is formed on the socket.

9. A method of controlling moisture in prosthetic socket system, the method comprising:
   positioning an air-impermeable liner on a lower part of a residual limb of a user;
   positioning a wicking material separate from the liner and on an outer surface of the liner, the wicking material being repeatedly installable on the outer surface of the liner;
   supplying at least one cooling fluid to the wicking material;
   positioning the lower part of the residual limb, the liner, the wicking material, and the at least one cooling fluid in a socket cavity defined by a socket, wherein a substantially sealed volume is defined between at least a portion of the liner and a corresponding portion of the socket, the wicking material carrying a supply of the at least one cooling fluid sized and configured such that the at least one cooling fluid is available for boiling within the substantially sealed volume when a temperature of the residual limb exceeds a temperature of the at least one cooling fluid; and
   applying a vacuum to the substantially sealed volume for selectively boiling the cooling fluid within the substantially sealed volume during physical activity of the user such that heat from the residual limb is converted into latent heat of vaporization by the at least one cooling fluid for a cooling effect, wherein supplying the at least one cooling fluid to the wicking material includes supplying the at least one cooling fluid to the wicking material via an aperture defined in a sidewall of the socket.

10. The method of claim 9, further comprising expelling gases produced by boiling the at least one cooling fluid via the second aperture defined in the socket.

11. The method of claim 9, wherein the at least one cooling fluid comprises an alcohol.

12. The method of claim 9, wherein the at least one cooling fluid comprises a mixture of an alcohol and water.

13. The method of claim 9, wherein the vacuum applied to the substantially sealed volume exhaust gases raising from the at least one cooling fluid from the substantially sealed volume.

14. The method of claim 9, further comprising a seal element positionable between the liner and the socket, wherein the seal element at least in part defines the substantially sealed volume.

15. The method of claim 14, wherein the seal element is formed on the liner.

16. The method of claim 14, wherein the seal element is formed on the socket.

* * * * *